United States Patent
Mitchinson et al.

(10) Patent No.: US 6,268,328 B1
(45) Date of Patent: Jul. 31, 2001

(54) VARIANT EGIII-LIKE CELLULASE COMPOSITIONS

(75) Inventors: Colin Mitchinson, Half Moon Bay; Dan J. Wendt, Walnut Creek, both of CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/216,295

(22) Filed: Dec. 18, 1998

(51) Int. Cl.[7] .............................. C11D 3/386; C12N 9/42; C12N 9/00

(52) U.S. Cl. .................. 510/392; 510/320; 510/321; 510/530; 8/181; 8/401; 8/137; 8/116.1; 162/95; 435/209

(58) Field of Search ...................... 510/320, 321, 510/392, 530, 226; 8/181, 401, 137, 116.1; 162/95; 435/209

(56) References Cited

U.S. PATENT DOCUMENTS

| | | | |
|---|---|---|---|
| 5,475,101 | 12/1995 | Ward et al. | 536/23.74 |
| 5,798,327 | * 8/1998 | Casteleijn et al. | 510/303 |
| 5,877,139 | * 3/1999 | Casteleijn et al. | 510/303 |
| 5,919,691 | * 7/1999 | Schuelein et al. | 435/209 |
| 6,001,639 | * 12/1999 | Schuelein et al. | 435/263 |
| 6,187,732 | * 2/2001 | Fowler et al. | 510/226 |

FOREIGN PATENT DOCUMENTS

| | | |
|---|---|---|
| 2075028 | 4/1981 | (GB) . |
| 2094826 | 3/1982 | (GB) . |
| 2095275 | 3/1982 | (GB) . |
| WO 91/04673 | 4/1991 | (WO) . |
| WO 92/16687 | 10/1992 | (WO) . |
| WO 93/20208 | 10/1993 | (WO) . |
| WO 93/20209 | 10/1993 | (WO) . |
| WO 94/14953 | 7/1994 | (WO) . |
| WO 94/21801 A | 9/1994 | (WO) . |
| WO 98/12307 A | 3/1998 | (WO) . |
| WO 00/14206 A | 3/2000 | (WO) . |
| WO 00/14208 A | 3/2000 | (WO) . |

OTHER PUBLICATIONS

Hreggvidsson et al., "An Extremely Thermostable Cellulase from the Thermophilic Eubacterium *Rhodothermus marinus*," *Appl. Environ. Microb.*, vol. 62, No. 8, pp. 3047–3049 (1996).

Knowles, J. et al., "Cellulase families and their genes," *TIBTECH 5*, 255–261, (1987).

Ooi et al., "Cloning and sequence analysis of a CDNA for cellulase (FI–CMCase) from *Aspergillus aculeatus*," *Curr. Genet.*, vol. 18, pp. 217–222 (1990).

Saartilahti et al., "CelS: a novel endoglucanase idenfitied from *Erwinia carotovora* subsp. *carotovora*," *Gene*, vol. 90, pp. 9–14 (1990).

Sakamoto et al., "Cloning and sequencing of cellulase cDNA from *Aspergillus kawachii* and its expression in *Saccharomyces cerevisiae*," *Curr. Genet.*, vol. 27, pp. 435–439 (1995).

Schulein et al., "[25] Cellulases of *Trichoderma reesei*," *Methods in Enzymology*, 160, 25, pp. 234–242, (1988).

PCT Search Report.

* cited by examiner

Primary Examiner—Yogendra N. Gupta
Assistant Examiner—Eisa Elhilo
(74) *Attorney, Agent, or Firm*—Genencor International, Inc.

(57) ABSTRACT

The present invention relates to novel variant EGIII or EGIII-like cellulases which have improved stability. The variant cellulases have performance sensitive residues replaced to a residue having improved stability.

20 Claims, 7 Drawing Sheets

Amino Acid Sequence of Mature EGIII Protein

```
5    QTSCDQWATFTGNGYTVSNNLWGASAGSGFGCVTAVSLSGGASWHADWQWSGGQNNVKSY  60
     QNSQIAIPQKRTVNSISSMPTTASWSYSGSNIRANVAYDLFTAANPNHVTYSGDYELMIW  120
     LGKYGDIGPIGSSQGTVNVGGQSWTLYYGYNGAMQVYSFVAQTNTTNYSGDVKNFFNYLR  180
     DNKGYNAAGQYVLSYQFGTEPFTGSGTLNVASWTASIN                       218
```

FIGURE 1

DNA Sequence of EGIII Without Introns

ATGAAGTTCCTTCAAGTCCTCCCTGCCCTCATACCGGCCGCCCTGGCCCAAACCAGC

TGTGACCAGTGGGCAACCTTCACTGGCAACGGCTACACAGTCAGCAACAACCTTTGG

GGAGCATCAGCCGGCTCTGGATTTGGCTGCGTGACGGCGGTATCGCTCAGCGGCGGG

GCCTCCTGGCACGCAGACTGGCAGTGGTCCGGCGGCCAGAACAACGTCAAGTCGTAC

CAGAACTCTCAGATTGCCATTCCCCAGAAGAGGACCGTCAACAGCATCAGCAGCATG

CCCACCACTGCCAGCTGGAGCTACAGCGGGAGCAACATCCGCGCTAATGTTGCGTAT

GACTTGTTCACCGCAGCCAACCCGAATCATGTCACGTACTCGGGAGACTACGAACTC

ATGATCTGGCTTGGCAAATACGGCGATATTGGGCCGATTGGGTCCTCACAGGGAACA

GTCAACGTCGGTGGCCAGAGCTGGACGCTCTACTATGGCTACAACGGAGCCATGCAA

GTCTATTCCTTTGTGGCCCAGACCAACACTACCAACTACAGCGGAGATGTCAAGAAC

TTCTTCAATTATCTCCGAGACAATAAAGGATACAACGCTGCAGGCCAATATGTTCTT

AGCTACCAATTTGGTACCGAGCCCTTCACGGGCAGTGGAACTCTGAACGTCGCATCC

TGGACCGCATCTATCAAC

FIGURE 2

```
                              1                                                              60
            T._reesei         M.........KF.LQVLPALIPAALAQTS...............CDQWATFTGNG..YTV
       H._schweinitzii        M.........KF.LQVLPAILPAALAQTS...............CDQYATFSGNG..YIV
        A._aculeatus__*       M.........KAFHL.LAALAGAAVAQQAQ.............LCDQYATYTGGV..YTI
         A._kawachii__*       M.........KLSMT.LSLFAATAMGQT...............MCSQYDSASSPP..YSV
         A._kawachii_2        M.........KAFHL.LAALSGAAVAQQAQ.............LCDQYATYTGGV..YTI
          A._oryzae__*        M.........KLSLA.LATLVATAFSQE...............LCAQYDSASSPP..YSV
            H._grisei         M........LKSALLLGAAAVSVQSASIPTIPANLEPRQIR.SLCELYGYWSGNG..YEL
        H._insolens__*        M........LKSALLLGPAAVSVQSASIPTIPANLEPRQIR.SLCELYGYWSGNG..YEL
   Chaetomium_brasiliense     M.........KLTLVLFVSSLA......AATPLGWRERQQQVSLCGQSSSWSGNG..YQL
            F._equseti        M.........KSTLLLAGAFAPLAFAKD...............LCEQYGYLSSDG..YSL
          F._javanicum_1      M.........KSAIVA.ALAGLAAASPTRLIPRGQ........FCGQWDSETAGA..YTI
          F._javanicum_2      M.........K..FFGVVSASLAATAVATPTTPTETIEKRDTTWCDAFGSLATSG..YTV
           G._roseum_Rj_1     M.........KANIVILSLFAPLAAVAQT..............LCGQYSSNTQGG..YIF
           G._roseum_Rj_2     M.........KSIISFFGLATLVAAAPSQNPTRTQPLEKRATTLCGQWDSVETGG..YTI
           G._roseum_PA_3     M.........KFQLLSLTAFAPLSLAA................LCGQYQSQSQGG..YIF
           G._roseum_Rj_4     M.........KTGIAYLAAVLPLA.MAES..............LCDQYAYLSRDG..YNF
       Memnoniella_echinata   M.........KVAAL.LVALSPLAF.AQS..............LCDQYSYYSSNG..YEF
       Emericella_desertoru   M.........K..LLALSLVSLASAASAASIL.SNTFTRRSD.FCGQWDTATVGN..FIV
         Actinomycete_11AG8   MRS......HPRS..ATM.TVLVVLASLGALLTAAAPAQANQQICDRYGTTTIQD.RYVV
         S._lividans_CelB__*  MRTLRPQARAPRGLLAALGAVLAAFALVSSLVTAAAPAQADTTICEPFGTTTIQG.RYVV
      Rhodothermus_marinus__* MNVMR..AVLVLSLLLLFGCDWL.FPDGDNGKEPEPEPEPTVELCGRWDARDVAGGRYRV
        Erwinia_carot___*     MQTVNTQPHRIFRVLLPAVFSSLLLSSLTVSAASSSNDADKLYF.........GNNKYYL 61                                                             120
            T._reesei         SNNLWGASAGSGF..GCV.TAVSLSGG.ASWHADWQWSGGQNNVKSYQNS..........
       H._schweinitzii        SNNLWGASAGSGF..GCV.TSVSLNGA.ASWHADWQWSGGQNNVKSYQNV..........
        A._aculeatus__*       NNNLWGKDAGSG..SQCTTVNSASSAG.TSWSTKWNWSGGENSVKSYANS..........
         A._kawachii__*       NQNLWGEYQGTG..SQCVYVDKLSSSG.ASWHTKWTWSGGEGTVKSYSNS..........
         A._kawachii_2        NNNLWGKDAGSG..SQCTTVNSASSAG.TSWSTKWNWSGGENSVKSYANS..........
          A._oryzae__*        NNNLWGQDSGTGFTSQCVYVDNLSSSG.AAWHTTWTWNGGEGSVKSYSNS..........
            H._grisei         LNNLWGKDTATS.GWQCTYLDGTNNGG.IQWNTAWEWQGAPDNVKNYPYV..........
        H._insolens__*        LNNLWGKDTATS.GWQCTYLDGTNNGG.IQWSTAWEWQGAPDNVKSYPYV..........
   Chaetomium_brasiliense     NNNLWGQSRATS.GSQCTYLDSSSNSG.IHWHTTWTWEGGEGEVKSYAYS..........
            F._equseti        NNNVWGKDSGTGD..QCTHVNWNNANG.AGWDVEWNWSGGKDNVKSYPNS..........
          F._javanicum_1      YNNLWGKDNAES.GEQCTTNSGEQSDGSIAWSVEWSWTGGQGQVKSYPNA..........
          F._javanicum_2      YHNNWGKGDATS.GSQCTTFTSVSNNNFV.WSTSWTWAGGAGKVKSYSNV..........
           G._roseum_Rj_1     NNNMWGMGSGSGS..QCTYVDKVWAEG.VAWHTDWSWSGGDNNVKSYPYS..........
           G._roseum_Rj_2     YNNLWGQDNG.S.GSQCLTVEGV.TDGLAAWSSTWSWSGGSSSVKSYSNA..........
           G._roseum_PA_3     NNNKWGQGSGSGS..QCLTIDKTWDSN.VAFHADWSWSGGTNNVKSYPNA..........
           G._roseum_Rj_4     NNNEWGAATGTGD..QCTYVDSTSSGG.VSWHSDWTWSGSESEIKSYPYS..........
       Memnoniella_echinata   NNNMWGRNSGQGN..QCTYVDYSSPNG.VGWRVNWNWSGGDNNVKSYPYS..........
       Emericella_desertoru   YNNLWGQDNADS.GSQ..TGVDSANGNSISWHTTWSWSGGSSSVKSYANA..........
         Actinomycete_11AG8   QNNRWGTSAT.....QCINVT..GNGFEITQADGS..VPTNGAPKSYPSVYDGCHYG...
         S._lividans_CelB__*  QNNRWGSTAP.....QCVTAT..DTGFRVTQADGS..APTNGAPKSYPSVFNGCHYT...
      Rhodothermus_marinus__* INNVWGAETA.....QCIEVGLETGNFTITRADHD..NGNNVA..AYPAIYFGCHWAPAR
        Erwinia_carot___*     FNNVWGKDEIKGWQQTIFYNSPISMG....WN..WHWPSSTHSVKAYPSLVSGWHWTAG.
```

FIGURE 3A

```
                              121                                                          180
             T._reesei       .QIAIP.QKRTVNSISSMPTTASW...SYSGSNIRANVAYDL.FTAANPNHVTYSGDYEL
         H._schweinitzii     .QINIP.QKRTVNSIGSMPTTASW...SYSGSDIRANVAYDL.FTAANPNHVTYSGDYEL
          A._aculeatus__*    .GLTF..NKKLVSQISQIPTTARW.S..YDNTGIRADVAYDL.FTAADINHVTWSGDYEL
          A._kawachii__*     .GLTF..DKKLVSDVSSIPTSVTW.SQD..DTNVQADVSYDL.FTAANADHATSSGDYEL
          A._kawachii_2      .GLSF..NKKLVSQISHIPTAARW.S..YDNTCIRRGRAYDL.FTAADINHVTWSGDYEL
           A._oryzae__*      .AVTF..DKKLVSDVQSIPTDVEW.SQDFTNTNVNADVAYDL.FTAADQNHVTYSGDYEL
              H._grisei      .GKQIQRGRK.ISDINSMRTSVSW...TYDRTDLRANVAYDV.FTARDPDHPNWGGDYEL
          H._insolens__*     .GKQIQRGRK.ISDINSMRTSVSW...TYDRTDIRANVAYDV.FTARDPDHPNWGGDYEL
     Chaetomium_brasiliense  .GRQVSTGLT.IASIDSMQTSVSW...EYNTTDIQANVAYDI.FTAEDPDHEHSSGDYEL
              F._equseti     .ALLIGEDKKTISSITNMQSTAEW...KYSGDNLRADVAYDL.FTAADPNHETSSGEYEL
          F._javanicum_1     .VVEI..EKKTLGEVSSIPSA..W.DWTYTGNGIIANVAYDL.FTSSTESGDA...EYEF
          F._javanicum_2     .ALEK..INKKISDIKSVSTR..W.IWRYTGTKMIANVSYDL.WFAPTASSNN...AYEI
           G._roseum_Rj_1    .GRELGT.KRIVSSIKSISSGADW...DYTGSNLRANAAYDI.FTSANPNHATSSGDYEV
           G._roseum_Rj_2    .VLSA..EAARISAISSIPSK..W.EWSYTGTDIVANVAYDL.FSNTDCGDTP...EYEI
           G._roseum_PA_3    .GLEFSR.GKKVSSIGTINGGADW...DYSGSNIRANVAYGI.FTSADPNHVTSSGDYEL
           G._roseum_Rj_4    .GLDLPE.KKIVTSIGSISTGAEW...SYSGSDIRADVAYDT.FTAADPNHATSSGDYEV
       Memnoniella_echinata  .GRQLPT.KRIVSWIGSLPTTVSW...NYQGNNLRANVAYDL.FTAANPNHPNSSGDYEL
       Emericella_desertoru  .AYQF..TSTKLNSLSSIPTS..W.KWQYSTTDIVANVAYDL.FTSSSAGGDS...EYEI
        Actinomycete_11AG8   ...NCAPRTTLPMRISSIGSAPSSVSYRYTGNGVY.NAAYDIWLDPTPRTNGVNR..TEI
         S._lividans_CelB__* ...NCSPGTDLPVRLDTVSAAPSSISYGFVDGAVY.NASYDIWLDPTARTDGVNQ..TEI
       Rhodothermus_marinus__* AIRDCAARAGAVRRAHELDVTP.......ITTGRW.NAAYDIWFSPVTNSGNGYSGGAEL
          Erwinia_carot___*  ....YTENSGLPIQLSSNKSITSNVTYSIKATGTY.NAAYDIWFHTTDKANWDSSPTDEL 181                                                          240
             T._reesei       MIWLGKYGDIGPIGSS....QGTVNVGGQSWTLYYGYNGAMQV......YSFVAQT.NTT
         H._schweinitzii     MIWLGKYGDIGPIGSS....QGTVNVGGQTWTLYYGYNGAMQV......YSFVAQS.NTT
          A._aculeatus__*    MIWLARYGGVQPIGSQ....IATATVDGQTWELWYG......ANGSQKTYSFVAPT.PIT
          A._kawachii__*     MIWLARYGSVQPIGKQ....IATATVGGKSWEVW..YGTSTQAGAEQKTYSFVAGS.PIN
          A._kawachii_2      MIWLARYGGVQPLGSQ....IATATVEGQTWELWYG......VNGAQKTYSFVAAN.PIT
           A._oryzae__*      MIWLARYGTIQPIGTQ....IDTATVEGHTWELWFTYGTTIQAGAEQKTYSFVSAT.PIN
              H._grisei      MIWLARYGGIYPIGTF....HSQVNLAGRTWDLWTGYNGNMRV......YSFLPPSGDIR
          H._insolens__*     MIWLARYGGIYPIGTF....HSQVNLAGRTWDLWTGYNGNMRV......YSFLPPSGDIR
     Chaetomium_brasiliense  MIWLARYNNVSPIGSS....VATATVGGDTWDLFAGANGDMEV......YSFVAENT.MN
              F._equseti     MVWLARIGGVQPIGSL....QTSVTIEGHTWELWVGMNGSMKV......FSFVAPT.PVN
          F._javanicum_1     MIWLSALGGAGPISNDGSP.VATAELAGTSWKLYQGKNNQMTV......FSFVAESDV.N
          F._javanicum_2     MIWVGAYGGALPISTPGKGVIDRPTLAGIPWDVYKGPNGDVTV......ISFVASSNQ.G
           G._roseum_Rj_1    MIWLANLGGLTPIGSP....IGTVKAAGRDWELWDGYNGAMRV......YSFVAPS.QLN
           G._roseum_Rj_2    MIWLSALGGAGPISSTGSS.IATVTIAGASWNLWQGQNNQMAV......FSFVAESDQ.K
           G._roseum_PA_3    MIWLGKLGDIYPIGNS....IGRVEAANREWDFLVGYNGAMKV......YSFVAPS.PVT
           G._roseum_Rj_4    MIWLANLGGLTPIGSP....IGTVKAAGRDWELWDGYNGAMRV......YSFVAPS.QLN
       Memnoniella_echinata  MIWLGRLGNVYPIGNQ....VATVNIAGQQWNLYYGYNGAMQV......YSFVSPN.QLN
       Emericella_desertoru  MIWLAALGGAGPISSTGSS.IATVTLGGVTWSLYSGPNGSMQV......YSFVASSTT.E
        Actinomycete_11AG8   MIWFNRVGPVQPIGSP....VGTAHVGGRSWEVWTGSNGSNDVI......SFLAPSA.IS
         S._lividans_CelB__* MIWFNRVGPIQPIGSP....VGTASVGGRTWEVWSGGNGSNDVL......SFVAPSA.IS
       Rhodothermus_marinus__* MIWLNWNGGVMPGGSR....VATVELAGATWEVWYADWDWNYIA......YRRTTPT.TS
          Erwinia_carot___*  MIWLNDTNA.....GPAGDYIETVFLGDSSWNVFKGWINADN.GGGWNVFSFVHTSGTNS
```

FIGURE 3B

```
                             241                                                          300
              T._reesei      NYSGDVKNFFNYLRDNKGYNAAGQYV..LSYQFGTEPF..TGSGT.LNVASWTASI.N..
         H._schweinitzii     SYSGDVKNFFNYLRDNKGYNAGGQYV..LSYQFGTEPF..TGSGT.LNVASWTASI.N..
           A._aculeatus__*   SFQGDVNDFFKYLTQNHGFPASSQYLI..TLQFGTEPF..TGGPATLSVSNWSASVQQAG
           A._kawachii__*    SWSGDIKDFFNYLTQNQGFPASSQHLI..TLQCGTEPF..TGGPATFTVDNWTASVN...
            A._kawachii_2    SFQGDINDFFKYLTQNHGFPASSQYLIILALQFGTEPF..TGGPATLNVADWSASVQ...
             A._oryzae__*    TFGGDIKKFFDYITSKHSFPASAQYLI..NMQFGTEPFFTTGGPVTFTVPNWTASVN...
                H._grisei    DFSCDIKDFFNYLERNHGYPAREQNLIV..YQVGTECF..TGGPARFTCRDFRADL....
              H._insolens__* DFSCDIKDFFNYLERNHGYPAREQNLIV..YQVGTECF..TGGPARFTCRDFRADL....
     Chaetomium_brasiliense  SFSGDVKDFFDYLEQNVGFPVDDQYLLV..FELGSEAF..TGGPATLSVSQFSANI....
               F._equseti    NFNADIKQFWDYLTKSQNFPADNQYL..LTFQFGTEPF..TGDNAKFTVTNFNAHLK...
              F._javanicum_1 NFCGDLADFTDYLVDNHGVSSSQ...ILQSVGAGTEPF..EGTNAVFTTNNYHADVE...
              F._javanicum_2 NFQADLKEFLNYLTSKQGLPSNY...VATSFQAGTEPF..EGTNAVLKTSAYTISVN...
              G._roseum_Rj_1 SFDGEIMDFFYVVKDMRGFPADSQHL..LTVQFGTEPI..SGSGAKFSVSHWSAKLG...
              G._roseum_Rj_2 SFSGDLNDFIQYLVDSQGYSGSQ...CLYSIGAGTEPF..TGTDAEFITTGYSVSVSAGD
              G._roseum_PA_3 LFDGNIMDFFYVMRDMQGYPMDKQYL..LSLQFGTEPF..TGSNANFSCWYFGAKIK...
              G._roseum_Rj_4 SFDGEIMDFFYVVKDMRGFPADSQHL..LTVQFGTEPI..SGSGAKFSVSHWSAKLG...
       Memnoniella_echinata  YFSGNVKDFFTYLQYNRAYPADSQYL..ITYQFGTEPF..TGQNAVFTVSNWSAQQNN..
        Emericella_desertoru SFSADLMDFINYLAENQGLSSSQ...YLTHVQAGTEPF..TGTDATLTVSSYSVSVS...
         Actinomycete_11AG8  SWSFDVKDFVD.QAVSHGLATPDWYLT..SIQAGFEPW...EGGTGLAVNSFSSAVNAG.
           S._lividans_CelB__* GWSFDVMDFVR.ATVARGLAENDWYLT..SVQAGFEPW...QNGAGLAVNSFSSTVETGT
       Rhodothermus_marinus__* VSELDLKAFID.DAVARGYIRPEWYLH..AVETGFELW...EGGAGLRTADFSVTVQ...
            Erwinia_carot___* A.SLNIRHFTDYLVQTKQWMSDEKYIS..SVEFGTEIF...GGDGQIDITEWRVDVK...

301                                                          360
              T._reesei      ............................................................
         H._schweinitzii     ............................................................
           A._aculeatus__*   F.............................................EPWQNGAGLAVNSF....
           A._kawachii__*    ............................................................
            A._kawachii_2    ............................................................
             A._oryzae__*    ............................................................
                H._grisei    .........................................................W..
              H._insolens__* .........................................................W..
     Chaetomium_brasiliense  ..........................................................A.
               F._equseti    ............................................................
              F._javanicum_1 ............................................................
              F._javanicum_2 ............................................................
              G._roseum_Rj_1 ............................................................
              G._roseum_Rj_2 SGCDETTTSSQAQSSTVETSTATQPQS...SSTVVPTVTLS.QPSNESTTTPVQSQ....
              G._roseum_PA_3 ............................................................
              G._roseum_Rj_4 ............................................................
       Memnoniella_echinata  ............................................................
        Emericella_desertoru ............................................................
         Actinomycete_11AG8  ..GGNGGTPGTPAACQVSYSTHTWPGGFTVDTTITNTGSTPVDGWELDFTLPAGHTVTSA
           S._lividans_CelB__* PGGTDPGDPGGPSACAVSYGTNVWQDGFTADVTVTNTGTAPVDGWQLAFTLPSGQRITNA
       Rhodothermus_marinus__* ............................................................
            Erwinia_carot___* ............................................................
```

FIGURE 3C

```
                              361
419
            T._reesei        ..........................................................
      H._schweinitzii        ..........................................................
        A._aculeatus__*      ......SSTV................................................
         A._kawachii__*      ..........................................................
         A._kawachii_2       ..........................................................
          A._oryzae__*       ..........................................................
            H._grisei        ..........................................................
         H._insolens__*      ..........................................................
Chaetomium_brasiliense       ..........................................................
            F._equseti       ..........................................................
         F._javanicum_1      .........................................................Y
         F._javanicum_2      ..........................................................
         G._roseum_Rj_1      ..........................................................
         G._roseum_Rj_2      ......PSSVETTPTAQPQSSSVQTTTTAQA....QPTSGTGCSRRRKRR......AVV
         G._roseum_PA_3      ..........................................................
         G._roseum_Rj_4      ..........................................................
   Memnoniella_echinata      ..........................................................
    Emericella_desertoru     ..........................................................
        Actinomycete_11AG8   WNALISPASGAVTARSTGSNGRIAANGGTQSFGFQGTSSGTGFNAPAGGRLNGTSCTVR
         S._lividans_CelB__* WNASLTPSSGSVTATGASHNARIAP.GGSLSFGFQGTYGGA.FAEPTGFRLNGTACTTV
    Rhodothermus_marinus__*  ..........................................................
         Erwinia_carot___*   ..........................................................
```

FIGURE 3D

```
                                                                      **    *  *      *
                      1                                               50
   H_insolens   MLKSALLLGP AAVSVQSASI PTIPANLEPR QIRSLCELYG YWSGNGYELL
     H_grisea   MLKSALLLGA AAVSVQSASI PTIPANLEPR QIRSLCELYG YWSGNGYELL
    eg3protein  ---------- ------MKFL QVLPALIPAA LAQTSCDQWA TFTGNGYTVS
H_schweinitzii  ---------- ------MKFL QVLPAILPAA LAQTSCDQYA TFSGNGYIVS
    M_echinada  ---------- ------MKVA ALLVALSPLA FAQSLCDQYS YYSSNGYEFN
   F_javanicum1 -------MKS AIVAALAGLA AASPTRLIPR GQ..FCGQWD SETAGAYTIY
    E_desertarou --MKLLALSL VSLASAASAA SILSNTFTRR SD..FCGQWD TATVGNFIVY
   F_javanicum2 --MKFFGVVS ASLAATAVAT PTTPTETIEK RDTTWCDAFG SLATSGYTVY
                  *  *     **   *      *  *    ** *           *  **

51                                              100
   H_insolens   NNLWGKDTAT SGWQC.TYLD GTNNGGIQWS TAWEWQGAPD NVKSYPYVGK
     H_grisea   NNLWGKDTAT SGWQC.TYLD GTNNGGIQWN TAWEWQGAPD NVKNYPYVGK
    eg3protein  NNLWGA.SAG SGFG..V.TA VSLSGGASW  ADWQWSGGQN NVKSYQNSQI
H_schweinitzii  NNLWGA.SAG SGFGC.V.TS VSLNGAASWH ADWQWSGGQN NVKSYQNVQI
    M_echinada  NNMWGR.NSG QGNQC.TYVD YSSPNGVGWR VNWNWSGGDN NVKSYPYSGR
   F_javanicum1 NNLWGKDNAE SGEQCTTNSG EQSDGSIAWS VEWSWTGGQG QVKSYPNAVV
    E_desertarou NNLWGQDNAD SGSQTGVDSA ..NGNSISWH TTWSWSGGSS SVKSYANAAY
   F_javanicum2 HNNWGKGDAT SGSQCTTFTS VSNNNFV.WS TSWTWAGGAG KVKSYSNVAL
                *  *                   *   *                  ***

101                                             150
   H_insolens   QIQRGRKISD INSMRTSVSW TYDRTDIRAN VAYDVFTARD PDHPNWGGDY
     H_grisea   QIQRGRKISD INSMRTSVSW TYDRTDLRAN VAYDVFTARD PDHPNWGGDY
    eg3protein  AIPQKRTVNS ISSMPTTASW SYSGSNIRAN VAYDLFTAAN PN VTYSGDY
H_schweinitzii  NIPQKRTVNS IGSMPTTASW SYSGSDIRAN VAYDLFTAAN PNHVTYSGDY
    M_echinada  QLPTKRIVSW IGSLPTTVSW NYQGNNLRAN VAYDLFTAAN PNHPNSSGDY
   F_javanicum1 EI.EKKTLGE VSSIPSAWDW TYTGNGIIAN VAYDLFTSST ...ESGDAEY
    E_desertarou QF.TSTKLNS LSSIPTSWKW QYSTTDIVAN VAYDLFTSSS ...AGGDSEY
   F_javanicum2 EK.INKKISD IKSVSTRWIW RYTGTKMIAN VSYDLWFAPT ...ASSNNAY
                   *         *   ***         *          *

151                                             200
   H_insolens   ELMIWLARYG GIYPIGTFHS QV....NLAG RTWDLWTGYN GNMRVYSFLP
     H_grisea   ELMIWLARYG GIYPIGTFHS QV....NLAG RTWDLWTGYN GNMRVYSFLP
    eg3protein  ELMIWLGKYG DIGPIGSSQG TV....NVGG QSWTLYYGYN GAMQVYSFVA
H_schweinitzii  ELMIWLGKYG DIGPIGSSQG TV....NVGG QTWTLYYGYN GAMQVYSFVA
    M_echinada  ELMIWLGRLG NVYPIGNQVA TV....NIAG QQWNLYYGYN GAMQVYSFVS
   F_javanicum1 EFMIWLSALG GAGPISNDGS PVA.TAELAG TSWKLYQGKN NQMTVFSFVA
    E_desertarou EIMIWLAALG GAGPISSTGS SIA.TVTLGG VTWSLYSGPN GSMQVYSFVA
   F_javanicum2 EIMIWVGAYG GALPISTPGK GVIDRPTLAG IPWDVYKGPN GDVTVISFVA
                 * * *       *         *     *  **   **       ***  *

201                                             250
   H_insolens   PSGDIRDFSC DIKDFFNYLE RNHGYPAREQ NLIVYQVGTE CFTGGPARFT
     H_grisea   PSGDIRDFSC DIKDFFNYLE RNHGYPAREQ NLIVYQVGTE CFTGGPARFT
    eg3protein  QT.NTTNYSG DVKNFFNYLR DNKGYNAAGQ YVLSYQFGTE PFTG.SGTLN
H_schweinitzii  QS.NTTSYSG DVKNFFNYLR DNKGYNAGGQ YVLSYQFGTE PFTG.SGTLN
    M_echinada  PN.QLNYFSG NVKDFFTYLQ YNRAYPADSQ YLITYQFGTE PFTGQNAVFT
   F_javanicum1 ES.DVNNFCG DLADFTDYLV DNHGVSS.SQ ILQSVGAGTE PFEGTNAVFT
    E_desertarou SS.TTESFSA DLMDFINYLA ENQGLSS.SQ YLTHVQAGTE PFTGTDATLT
   F_javanicum2 SS.NQGNFQA DLKEFLNYLT SKQGLPS.NY VATSFQAGTE PFEGTNAVLK
                 *  *    *

251
   H_insolens   CRDFRADLW~
     H_grisea   CRDFRADLW~
    eg3protein  VASWTASIN~
H_schweinitzii  VASWTASIN~
    M_echinada  VSNWSAQQNN
   F_javanicum1 TNNYHADVEY
    E_desertarou VSSYSVSVS~
   F_javanicum2 TSAYTISVN~
```

FIGURE 4

VARIANT EGIII-LIKE CELLULASE COMPOSITIONS

BACKGROUND OF THE INVENTION

1. Field of the Invention

The present invention is directed to novel mutant cellulase compositions which have improved stability. More specifically, the present invention relates to a family of mutant cellulase enzymes from fungi and bacteria which are related in sequence to EGIII produced by *Trichoderma reesei*, but which have certain mutations which provide resistance to, for example, temperature stress.

2. State of the Art

Cellulases are enzymes which are capable of hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al., (1987), *TIBTECH* 5, 255–261); and are known to be produced by a large number of bacteria, yeasts and fungi.

Primary among the applications that have been developed for the use of cellulolytic enzymes are those involving degrading (wood)cellulose pulp into sugars for (bio)ethanol production, textile treatments like 'stone washing' and 'biopolishing', and in detergent compositions. Thus, cellulases are known to be useful in the treatment of mechanical pulp (see e.g., PCT Publication No. WO 92/16687). Additionally, cellulases are known to be useful as a feed additive (see e.g., PCT Publication No. WO 91/04673) and in grain wet milling.

Of primary importance, however, cellulases are used in the treatment of textiles, i.e., in detergent compositions for assisting in the removal of dirt or grayish cast (see e.g., Great Britain Application Nos. 2,075,028, 2,095,275 and 2,094,826 which illustrate improved cleaning performance when detergents incorporate cellulase) or in the treatment of textiles prior to sale to improve the feel and appearance of the textile. Thus, Great Britain Application No. 1,358,599 illustrates the use of cellulase in detergents to reduce the harshness of cotton containing fabrics and cellulases are used in the treatment of textiles to recondition used fabrics by making their colors more vibrant (see e.g., The Shizuoka Prefectural Hammamatsu Textile Industrial Research Institute Report, Vol. 24, pp. 54–61 (1986)). For example, repeated washing of cotton containing fabrics results in a grayish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Thus, cellulases have been shown to be effective in many industrial processes. Accordingly, there has been a trend in the field to search for specific cellulase compositions or components which have particularly effective performance profiles with respect to one or more specific applications. In this light, cellulases produced (expressed) in fungi and bacteria have been subject of attention. For example, cellulase produced by certain fungi such as Trichoderma spp. (especially *Trichoderma longibrachiatum*) have been given much attention because a complete cellulase system capable of degrading crystalline forms of cellulose is readily produced in large quantities via fermentation procedures. This specific cellulase complex has been extensively analyzed to determine the nature of its specific components and the ability of those components to perform in industrial processes. For example, Wood et al., "Methods in Enzymology", 160, 25, pages 234 et seq. (1988), disclose that complete fungal cellulase systems comprise several different enzyme classifications including those identified as exo-cellobiohydrolases (EC 3.2.1.91) ("CBH"), endoglucanases (EC 3.2.1.4) ("EG"), and β-glucosidases (EC 3.2.1.21) ("BG"). The fungal cellulase classifications of CBH, EG and BG can be further expanded to include multiple components within each classification. U.S. Pat. No. 5,475,101 (Ward et al.) discloses the purification and molecular cloning of one particularly useful enzyme called EGIII which is derived from *Trichoderma longibrachiatum*.

PCT Publication No. WO 94/14953 discloses endoglucanases which are encoded by a nucleic acid which comprises any one of a series of DNA sequences, each having 20 nucleotides.

Ooi et al., *Curr. Genet.*, Vol. 18, pp. 217–222 (1990) disclose the cDNA sequence coding for endoglucanase F1-CMC produced by *Aspergillus aculeatus* which contains the amino acid strings NNLWG, ELMIW and GTEPFT. Sakamoto et al., *Curr. Genet.*, Vol. 27, pp. 435-439 (1995) discloses the cCNA sequence encoding the endoglucanase CMCase-1 From *Aspergillus kawachii* IFO 4308 which contains the amino acid strings ELMIW and GTEPFT. Ward et al., discloses the sequence of EGIII having the amino acid strings NNLWG, ELMIW and GTEPFT. Additionally, two cellulase sequences, one from *Erwinia carotovara* and *Rhodothermus marinus* are disdosed in Saarilahti et al., *Gene*, Vol.90, pp.9–14 (1990) and Hreggvidsson et al., *Appl. Environ. Microb.*, Vol. 62, No. 8, pp.3047–3049 (1996) which contain the amino acid string ELMIW.

Despite knowledge in the art related to many cellulase compositions having applications in some or all of the above areas, there is a continued need for new cellulase compositions which have improved stability under conditions present in applications for which cellulases are useful, i.e., household detergents, stonewashing compositions or laundry detergents.

SUMMARY OF THE INVENTION

It is an object of the invention to provide for novel variant EGIII or EGIII-like cellulase compositions which have improved stability.

It is a further object of the invention to provide for novel variant EGIII or EGIII-like cellulase compositions which have improved performance under conditions of thermal stress.

It is a further object of the invention to provide for novel variant EGIII or EGIII-like cellulase containing compositions which will provide excellent performance in detergent applications, including laundry detergents.

It is a further object of the invention to provide for novel variant EGIII or EGIII-like cellulase containing compositions which have improved performance attributes for use in the textiles treatment field.

It is a further object of the invention to provide for novel variant EGIII or EGIII-like cellulase composition which have improved characteristics for the reduction of biomass, as an additive in animal feed, in starch processing and in baking applications.

According to the present invention, a variant EGIII or EGIII-like cellulase is provided wherein one or more amino acids are modified or deleted to confer improved performance, including stability in the presence of thermal and/or surfactant mediated stress. Preferably, the amino acids to be modified correspond in position to residues T2, S3, A8, F10, S18, A24, S25, F30, G31, V36, L38, A42, A46, D47, Q49, Q61, Q64, I65, A66, Q69, A83, S86, S90, V109, T110, Y111, K123, D126, S133, Q134, G135, V139, T145, Q162, N164, T166, Y168, N174, R180, K183, N186, A188, G189, V192, L193, S205, G206, N209, A211, T214 and/or I217 in EGIII from *Trichoderma reesei*. In another preferred embodiment, the amino acids to be modified correspond in position to residues T2S, S3(L/F), A8(S/D/G), F10(Y/E/A/W), S18(N/Y/L), A24(R/K/Q), S25((N/T), F30(N/E/S/W), G31Q, V36(Y/E/G), L38((S/N), A42((V/I), A46((V/T), D47(N/E/T/A), Q49(N/S/E), Q61(P/A), Q64(G/V/A), I65(R/V/Y/K), A66(Q/E), Q69(T/E/R), A83(V/W), S86(N/T/Q), S90(N/T), V109(P/E/A), T110(N/S/G), Y111(S/G/W), K123(R/A), D126(N/G), S133(Q/D/T/F), Q134(V/G/H), G135(A/S), V139(I/L), T145(N/K/S/D), Q162(P/E/S), N164(Q/D/T), T166(N/E/R), Y168F/W, N174D, R180(Q/V/A/E), K183(R/H/Q), N186(P/S), A188(D/R), G189(S/E), V192L, L193(I/Q/T), S205(N/D/P), G206A, N209T, A211(R/S/N), T214(S/H/R) and/or I217(Q/V/L) in EGIII. Most preferably, the modified amino acids correspond to A24(K/Q/R), G31Q, Q64(G/V/A), V139L, Y168F, N174D, V192L, G206A and/or N209T.

In another embodiment, the present invention provides for a variant EGIII or EGIII-like cellulase which has less stability than the EGIII or EGIII-like cellulases provided herein and has homology to EGIII at any of the residues identified herein for change.

In yet another embodiment, the substitution comprises an insertion of a residue between positions corresponding to positions 33 and 34 in EGIII or of equivalent positions in an EGIII-like enzyme comprising a tyrosine, asparagine or aspartic acid, or an insertion of a residue between positions 204 and 205 comprising glycine, glutamine or threonine.

In a preferred embodiment of the present invention, the variant EGIII or EGIII-like cellulase is an endoglucanase. Also preferably, the enzyme is derived from a fungal or bacterial source, most preferably from a filamentous fungus.

In another embodiment of the present invention, a DNA encoding the variant EGIII or EGIII-like cellulase according to the invention is provided. Also provided are expression vectors comprising that DNA, host cells transformed with such expression vectors and variant EGIII or EGIII-like cellulases produced by such host cells.

As shown in more detail below, the substitutions identified herein are important to the stability of EGIII and EGIII-like enzymes, particularly under thermal stress. Accordingly, it is within the scope of the present invention to use the EGIII or EGIII-like enzyme in textile treatment, e.g., in laundry detergent or stonewashing compositions, in the reduction of biomass, in the production of feed additives or treatment of feed, in the treatment of wood pulp for the production of paper or pulp based products, and in the treatment of starch during grain wet milling or dry milling to facilitate the production of glucose, high fructose corn syrup and/or alcohol.

BRIEF DESCRIPTION OF THE DRAWINGS

FIG. 1 illustrates the amino acid sequence of mature EGIII protein from *Trichoderma longibrachiatum* (*reesei*) (SEQ ID NO: 1) showing the residues described in accordance with the present invention.

FIG. 2 illustrates the DNA sequence of EGIII from *Trichoderma longibrachiatum* without introns (SEQ ID NO: 2).

FIG. 3 illustrates an alignment of the full length sequence of 20 EGIII-like cellulases in alignment with EGIII (SEQ ID NO: 3), indicating equivalent residues based on primary sequence modeling, including those derived from *Trichoderma reesei* (SEQ ID NO: 3), *Hypocrea schweinitzii* (SEQ ID NO: 4), *Aspergillus aculeatus* (SEQ ID NO: 5), *Aspergillus kawachii* (1) (SEQ ID NO: 6), *Aspergillus kawachii* (2) (SEQ ID NO: 7), *Aspergillus oryzae* (SEQ ID NO: 8), *Humicola grisea* (SEQ ID NO: 9), *Humicola insolens* (SEQ ID NO: 10), *Chaetomium brasiliense* (SEQ ID NO: 11), *Fusarium equseti* (SEQ ID NO: 12), *Fusarium javanicum* (1) (SEQ ID NO: 13), *Fusarium javanicum* (2) (SEQ ID NO: 14), *Gliociadium roseum* (1) (SEQ ID NO: 15), *Gliociadium roseum* (2) (SEQ ID NO: 16), *Gliocladium roseum* (3) (SEQ ID NO: 17), *Gliociadium roseum* (4) (SEQ ID NO: 18), *Memnonielia echinata* (SEQ ID NO: 19), *Emericella desertoru* (SEQ ID NO: 20), Actinomycete 1 1AG8 (SEQ ID NO: 21), *Streptomyces lividans* CeIB (SEQ ID NO: 22), *Rhodothermus marinus* (SEQ ID NO: 23) and *Erwina carotovara* (SEQ ID NO: 24).

FIG. 4 illustrates an alignment of the full length sequence of 7 EGIII-like cellulases in alignment with EGIII, indicating equivalent residues based on primary sequence modeling, including those derived from *Humicola insolens* (SEQ ID NO: 10), *Humicola grisea* (SEQ ID NO: 9), *Trichoderma reesei* (eg3 protein) (SEQ ID NO: 3), *Hypocrea schweinitzii* (SEQ ID NO: 4), *Memnonielia echinata* (SEQ ID NO: 19), *Fusarium javanicum* (1) (SEQ ID NO: 13), *Emericelia desertoru* (SEQ ID NO: 20) and *Fusarium javanicum* (2) (SEQ ID NO: 14).

DETAILED DESCRIPTION OF THE INVENTION

Applicants have isolated novel members of a family of cellulases which have homology to EGIII from *Trichoderma reesei*. Analysis of these cellulases has resulted in differential performance between the cellulases, despite significant homology. In particular, it was discovered that the EGIII-like cellulases from *Humicola insolens, Humicola grisea, Memnonella echinata, Fusarium javanicum* and *Emericella desertoru* have superior performance under conditions of thermal stress. By comparing the residues in these higher performance EGIII-like cellulases with that of EGIII, it is possible to identify residue differences between the more stable cellulases and EGIII, thus also identifying residues which are important for the improved thermal stability of the more stable EGIII-like cellulases. Accordingly, by optimizing the residues in the EGIII-like cellulases which differ from EGIII, it should be possible to further improve the thermal stability of the EGIII-like cellulases. Similarly, by comparing the residues in these relatively more stable EGIII-like cellulases with that of EGIII or less stable homologs, it is possible to identify residue differences between the more stable cellulases and EGIII or less stable EGIII-like cellulases, thus also identifying residues which are important for the improved thermal stability of the more stable EGIII-like cellulases. Accordingly, by changing these residues in EGIII or other less stable EGIII-like cellulases, it will be possible to further improve the thermal stability of EGIII. The present invention thus encompasses all such modifications which are enabled by the sequence comparison of EGIII-like cellulases together with stability data. Sequence alignments may be produced using different EGIII-like cellulases and may slightly differ from one alignment to another depending on the number of sequences and the degree of homology. Suitable experiments to determine appropriate modifications are routine to the ordinarily skilled worker in conjunction with the present disclosure.

Accordingly, the present invention relates to a variant EGIII or EGIII-like cellulase having improved stability, which cellulase is obtained from organisms which produce EGIII or EGIII-like cellulases. In a particularly preferred embodiment, the variant is characterized by having one or more residues as identified herein replaced with a residue conferring improved stability at that site. Preferably, the amino acids to be modified correspond in position to residues 2, 8, 10, 18, 24, 25, 30, 31, 36, 38, 42, 46, 47, 49, 61, 64, 65, 66, 69, 83, 86, 90, 109, 110, 111, 123, 126, 133, 134, 135, 139, 145, 162, 164, 166, 168, 174, 180, 183, 186, 188, 189, 192, 193, 304, 205, 206, 209, 211, 214 and/or 217 in EGIII from *Trichoderma reesei*. In another preferred embodiment, the amino acids to be modified correspond in position to residues T2S, S3(L/F), A8(S/D/G), F10(Y/E/A/W), S18(N/Y/L), A24(R/K/Q), S25((N/T), F30(N/E/S/W), G31Q, V36(Y/E/G), L38((S/N), A42((V/I), A46((V/T), D47 (N/E/T/A), Q49(N/S/E), Q61(P/A), Q64(G/V/A), I65(R/V/Y/K), A66(Q/E), Q69(T/E/R), A83(V/W), S86(N/T/Q), S90 (N/T), V109(P/E/A), T110(N/S/G), Y111(S/G/W), K123(R/A), D126(N/G), S133(Q/D/T/F), Q134(V/G/H), G135(A/S), V139(I/L), T145(N/K/S/D), Q162(P/E/S), N164(Q/D/T), T166(N/E/R), Y168F/W, N174D, R180(Q/V/A/E), K183(R/H/Q), N186(P/S), A188(D/R), G189(S/E), V192L, L193(I/Q/T), S205(N/D/P), G206A, N209T, A211(R/S/N), T214(S/H/R) and/or I217(Q/V/L) in EGIII. Most preferably, the modified amino acids correspond to A24(K/Q/R), G31Q, Q64(G/V/A), V139L, Y168F, N174D, V192L, G206A and/or N209T.

In another embodiment, the present invention provides for a variant EGIII or EGIII-like cellulase which has less stability than the EGIII or EGIII-like cellulases provided herein and has homology to EGIII at any of the residues identified herein for change.

In yet another embodiment, the substitution comprises an insertion of a residue between positions corresponding to positions 33 and 34 in EGIII or equivalent positions in an EGIII-like cellulase comprising a tyrosine, asparagine or aspartic acid, or an insertion of a residue between positions 204 and 205 comprising glycine, glutamine or threonine.

The residue to be modified should be changed to a residue which confers additional stability to the enzyme. The improved protein according to the present invention comprises an amino acid sequence which is derived from the amino acid sequence of a precursor protein. The precursor protein may be a naturally occurring protein or a recombinant protein. The amino acid sequence of the improved protein is derived from the precursor protein's amino acid sequence by the substitution, deletion or insertion of one or more amino acids of the precursor amino acid sequence. Such modification is generally of the precursor DNA sequence which encodes the amino acid sequence of the precursor proteins rather than manipulation of the precursor protein per se. Suitable methods for such manipulation of the precursor DNA sequence include methods disclosed herein and in commonly owned U.S. Pat. Nos. 4,760,025 and 5,185,258, incorporated herein by reference.

Within the specification, certain terms are disclosed which are defined below so as to clarify the nature of the claimed invention.

"Cellulase" is a well classified category of enzymes in the art and includes enzymes capable of hydrolyzing cellulose polymers to shorter cellooligosaccharide oligomers, cellobiose and/or glucose. Common examples of cellulase enzymes include exo-cellobiohydrolases and endoglucanases and are obtainable from many species of cellulolytic organisms, particularly including fungi and bacteria.

"EGIII" cellulase refers to the endoglucanase component described in Ward et al., U.S. Pat. No. 5,475,101 and Proceedings on the Second TRICEL Symposium on *Trichoderma Reesei* Cellulases And Other Hydrolases, Suominen & Reinikainen eds., Espoo Finland (1993), pp. 153–158 (Foundation for Biotechnical and Industrial Fermentation Research, Vol. 8). As discussed therein, EGIII is derived from *Trichoderma reesei* (*longibrachiatum*) and is characterized by a pH optimum of about 5.8, an isoelectric point (pI) of about 7.4 and a molecular weight of about 25 kD. The enzyme commonly referred to as EGII from *Trichoderma reesei* has been previously referred to in the literature by the nomenclature EGIII by some authors, but that enzyme differs substantially from the enzyme defined herein as EGIII in terms of molecular weight, pI and pH optimum.

"EG-III like enzyme", "EGIII-like protein" or "EGIII-like cellulase" according to the present invention means enzymes which are related to EGIII by having certain amino acid strings in common with EGIII. As used herein, EGIII-like cellulase is also intended to encompass EGIII from *Trichoderma reesei*. Thus an EGIII-like cellulase comprises an enzyme having cellulolytic activity which comprises an amino acid sequence comprising therein an amino acid string selected from the group consisting of one or more of:

(a) Asn-Asn-(Leu/Phe/Lys/Ile)-Trp-Gly (SEQ ID NO: 25);

(b) Glu-(Leu/Phe/Ile)-Met-Ile-Trp (SEQ ID NO: 26);

(c) Gly-Thr-Glu-Pro-Phe-Thr (SEQ ID NO: 27);

(d) (Ser/Try/Cys/Trp/Thr/Asn/Lys/Arg)-(Val/pro)-(Lys/Ala)-(Ser/Ala)-(Tyr/Phe) (SEQ ID NO: 28); and (e) Lys-Asn-Phe-Phe-Asn-Tyr (SEQ ID NO: 29).

In one embodiment, the enzyme of the invention further has a significant structural and/or sequence homology to EGIII. Thus, in one aspect of this embodiment of the invention, the enzyme has at least 30%, preferably at least 40% and most preferably at least 60% amino acid identity to EGIII. However, it should be recognized that homology alone is often not an appropriate measure for whether a particular enzyme identified by the methods described herein represents an EGIII-like enzyme. Accordingly, while homologous enzymes are indeed detected by the methods described and exemplified therein, the degree of homology should not be seen as limiting the scope of the invention.

It is contemplated that the EGIII-like cellulases of the invention may be found in many organisms which produce cellulases. However, likely sources of EGIII-like cellulase include those derived from a bacterial or fungal sources, and more particularly, from an Actinomycete, a Bacillus or a filamentous fungus. In a preferred embodiment, the cellulase is derived from the filamentous fungal family Metazoa, preferably Euascomycetes. Within Metazoa, fungal phylogenetic classifications which produce EGIII-like cellulases include the mitosporic Pyrenomycetes (including Acremonium), Sordariales (including Thielavia), Hypocreales (including Nectriaceae such as Fusarium, Necitia, Verticillium, Myrothecium and Gliocladium; and Hypocrea) and Eurotiales (including mitosporic Trichocomaceae such as Aspergillus and Penicillium).

The Euascomycete preferably belongs to Diaporthales, Halosphaeriales, Microascales, Ophiostomatales, Phyllachorales, Sordariales or Xylariales. Also preferably, the Eusacomycete belongs to Hypocreales comprising Clavicipitaceae, Melanosporaceae, Nectriaceae, Niessliaceae or Mitosporic Hypocreales. Further preferably, the Euascomycete belongs to Hypocreaceae, wherein said Hypocreaceae does not comprise Trichoderma. Most preferably, the Euascomycete is Gliocladium spp., Fusarium spp., Acremonium spp., Myceliophtora spp., Verticillium spp., Myrothecium spp., Penicillium spp., Chaetomium spp., Emercella spp., and Phanerochaete spp. Specific organisms which are contemplated as possessing EGIII-like cellulases include *Chaetomium thermophilum* var. therm., *Chaetomium atrobrunneum, Chaetomium brasiliense, Chaetomium globosum, Chaetomium vitellium, Paecilomyces lilacinus, Chaetomium thermophilum* var. dissitum, *Humicola insolens, Humicola brevis, Memnoniella echinata, Fusarium equiseti, Fusarium oxysporum, fusarium stilboides, Myceliophthora thermophila, Fusarium javanicum, Humicola grisea* var. thermoidea, *Stibella thermophila, Melanocarpus albomyces, Arthrobotrys superba, Myceliophthora hinunilea, Chaetomium pachypodiodes, Myrothecium verrucaria, Penicillium crysogenum, Malbranchea sulfurea, Lunulospora curvula, Emericella desertorum, Acremonium strictum, Cylindrocarpon heteronema*, and *Ulociadium chartarum*. Within the Actinomycetes, Streptomyces appears to possess EGIII-like cellulases.

EGIII-like cellulases according to the invention may be obtained according to the following methods. DNA primers are constructed which encode an amino acid sequence selected from the group consisting of one or more of:

(a) Asn-Asn-(Leu/Phe/Lys/lle)-Trp-Gly (SEQ ID NO: 25);

(b) Glu-(Leu/Phe/lle)-Met-lle-Trp (SEQ ID NO: 26);

(c) Gly-Thr-Glu-Pro-Phe-Thr (SEQ ID NO: 27);

(d) (Ser/Try/Cys/Trp/Thr/Asn/Lys/Arg)-(Val/pro)-(Lys/Ala)-(Ser/Ala)-(Tyr/Phe) (SEQ ID NO: 28); and (e) Lys-Asn-Phe-Phe-Asn-Tyr (SEQ ID NO: 29), and used to obtain DNA, and genes encoding enzymes having cellulolytic activity according to established methods. In addition, the EGIII of the invention may be obtained by methods conventional in molecular biology, e.g., PCR cloning, using one of the cellulase backbones identified herein as an EGIII-like cellulase.

In a preferred embodiment according to this aspect of the invention, degenerate primers are prepared corresponding to one or more of the above peptides. The peptides are combined with a genomic DNA from a target organism (i.e., the organism in which the EGIII-like cellulase is sought) under conditions suitable to initiate a standard PCR reaction. In this embodiment, it is advantageous to select degenerate primers corresponding to peptides (a) and/or (d) plus primers corresponding to (c) and/or (e) and perform PCR with those peptides. After the PCR reaction has been performed, the resulting DNA is run on a polyacrylamide gel and bands corresponding in size to the EGIII fragment comprising peptides (a) and/or (d) in addition to (c) and /or (e), i.e., those in the 400–1000 base pair range, are selected out. These fragments are pooled and reamplified using primers corresponding to peptides (a) and/or (d) plus primers corresponding to peptide (b) or, alternatively, using primers corresponding to peptide (c) and/or (e) plus primers corresponding to peptide (b). Strong bands of the expected size (in the case of EGIII-like cellulases, the bands will correspond to the approximately 250–500 base pair range) are excised and sequenced. The sequence is then used to design exact match primers and these primers used with the technique referred to as rapid amplification of genomic DNA ends to obtain the full length gene, see e.g., Mizobuchi et al., *BioTechniques*, Vol. 15, No. 2, pp 215–216 (1993).

However, it is also possible to use the degenerate DNA's as hybridization probes against a genomic library obtained from a target organism to analyze whether a given fragment correlates to a similar sequence in the target organism. A useful hybridization assay is as follows: Genomic DNA from a particular target source is fragmented by digestion with a restriction enzyme(s), e.g., EcoR I, Hind III, Bam HI, Cla I, Kpn I, Mlu I, Spe I, Bgl II, Nco I, Xba I, Xho I and Xma I (supplied by New England Biolabs, Inc., Beverly, Mass. and Boehringer Mannheim) according to the manufacturer's instructions. The samples are then electrophoresed through an agarose gel (such as, for example, 0.7% agarose) so that separation of DNA fragments can be visualized by size. The gel may be briefly rinsed in distilled $H_2O$ and subsequently depurinated in an appropriate solution (such as, for example, 0.25M HCl) with gentle shaking followed by denaturation for 30 minutes (in, for example, 0.4 M NaOH). A renaturation step may be included in which the gel is placed in 1.5 M NaCl, IM Tris, pH 7.0 with gentle shaking for 30 minutes. The DNA should then be transferred onto an appropriate positively charged membrane, for example the Maximum Strength Nytran Plus membrane (Schleicher & Schuell, Keene, N. H.), using a transfer solution (such as, for example, 6×SSC (900 mM NaCl, 90 mM trisodium citrate). After the transfer is complete, generally at about 2 hours or greater, the membrane is rinsed and air dried at room temperature after using a rinse solution (such as, for example, 2×SSC[2×SSC=300 mM NaCl, 30 mM trisodium citrate]). The membrane should then be prehybridized, (for approximately 2 hours or more) in a suitable prehybridization solution (such as, for example, an aqueous solution containing per 100 mls: 30–50 mls formamide, 25 mls of 20×SSPE (1×SSPE=0.18 M NaCl, 1 mM EDTA, 10 mM $NaH_2PO_4$, pH 7.7), 2.5 mls of 20% SDS, 1 ml of 10 mg/ml sheared herring sperm DNA).

A DNA probe corresponding to the peptide sequences above should be isolated by electrophoresis in an agarose gel, the fragment excised from the gel and recovered from the excised agarose. This purified fragment of DNA is then labeled (using, for example, the Megapnme labeling system according to the instructions of the manufacturer to incorporate $P^{32}$ in the DNA (Amersham International plc, Buckinghamshire, England)). The labeled probe is denatured by heating to 95° C. for 5 minutes and immediately added to the prehybridization solution above containing the membrane. The hybridization reaction should proceed for an appropriate time and under appropriate conditions, for example, for 18 hours at 37° C. with gentle shaking. The membrane is rinsed (for example, in 2×SSC/0.3% SDS) and then washed with an appropriate wash solution and with gentle agitation. The stringency desired will be a reflection of the conditions under which the membrane (filter) is washed.

Specifically, the stringency of a given reaction (i.e., the degree of homology necessary for successful hybridization) will largely depend on the washing conditions to which the filter from the Southern Blot is subjected after hybridization. "Low-stringency" conditions as defined herein will comprise washing a filter from a Southern Blot with a solution of 0.2×SSC/0.1% SDS at 20° C. for 15 minutes. Standard-stringency conditions comprise a further washing step comprising washing the filter from the Southern Blot a second time with a solution of 0.2×SSC/0.1% SDS at 37° C. for 30 minutes.

The DNA which hybridizes with the DNA primers outlined above and thus identified by this method a corresponding EGIII encoding gene may be isolated by routine methods and used to express the corresponding EGIII-like cellulase according to routine techniques. A preferred cloning procedure comprises the rapid amplification of genomic DNA ends described in, e.g., Mizobuchi et al., BioTechniques, Vol. 15, No. 2, pp. 215–216 (1993). Upon obtaining the cloned gene, routine methods for insertion of the DNA into a vector which can then be transformed into a suitable host cell are used. Culturing the transformed host cell under appropriate conditions then results in production of the EGIII-like cellulase which can be obtained, purified and prepared as necessary for a particular application.

The EGIII-like cellulases of the invention are preferably isolated or purified. In the context of the present invention, purification or isolation generally means that the EGIII-like cellulase is altered from its natural state by virtue of separating the EGIII-like cellulase from some or all of the naturally occurring substituents with which it is associated in nature, e.g., the source organism or other cellulases or enzymes expressed by the source organism in conjunction with the EGIII cellulase. Similarly, the EGIII-like cellulases of the invention may be combined with other components which are not naturally present in the natural state. Isolation of purification may be accomplished by art recognized separation techniques such as ion exchange chromatography, affinity chromatography, hydrophobic separation, dialysis, protease treatment, ammonium sulphate precipitation or other protein salt precipitation techniques, centrifugation, size exclusion chromatography, filtration, microfiltration, gel electrophoresis or separation on a gradient to remove whole cells, cell debris, impurities, extraneous proteins, or enzymes undesired in the final composition.

A residue in an EGIII-like cellulase which is "corresponding" or "equivalent" to a residue present in EGIII means a residue which exists in an equivalent position to that in EGIII, as indicated by primary sequence homology, tertiary structural homology (as shown by, i.e., crystal structure or computer modeling) or functional equivalence. A variant EGIII-like cellulase has an amino acid sequence which is derived from the amino acid sequence of a precursor EGIII-like cellulase. The precursor cellulases include naturally occurring cellulases and recombinant cellulases (as defined herein). The amino acid sequence of the EGIII-like cellulase variant is derived from the precursor EGIII-like cellulase amino acid sequence by the substitution, deletion or insertion of one or more amino acids of the precursor amino acid sequence. Such modification is of the precursor DNA sequence which encodes the amino acid sequence of the precursor cellulase rather than manipulation of the precursor cellulase enzyme per se. Suitable methods for such manipulation of the precursor DNA sequence include methods disclosed herein and in commonly owned U.S. Pat. Nos. 4,760,025 and 5,185,258. Specific residues corresponding to the positions which are responsible for instability in the presence of surfactant are identified herein for substitution or deletion. The amino acid position number (i.e., +11) refers to the number assigned to the mature *Trichoderma reesei* EGIII sequence presented in FIG. 1. The invention is directed to the mutation of EGIII-like cellulases which contain amino acid residues at positions which are equivalent to the particular identified residue in Trichoderma reesei EGIII. A residue (amino acid) of a precursor cellulase is equivalent to a residue of *Trichoderma reesei* EGIII if it is either homologous (i.e., corresponding in position in either primary or tertiary structure) or is functionally analogous to a specific residue or portion of that residue in *Trichoderma reesei* EGIII (i.e., having the same or similar functional capacity to combine, react, or interact chemically or structurally). As used herein, numbering is intended to correspond to that of the mature EGIII amino acid sequence as illustrated in FIG. 2.

"Cellulose containing fabric" means any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g. lyocell). Specifically included within the definition of cellulose containing fabric is any yarn or fiber made of such materials. Cellulose containing materials are often incorporated into blends with materials such as synthetic fibers and natural non-cellulosic fibers such as wool and silk.

"Cotton-containing fabric" means sewn or unsewn fabrics, yarns or fibers made of pure cotton or cotton blends including cotton woven fabrics, cotton knits, cotton denims, cotton yarns, raw cotton and the like. When cotton blends are employed, the amount of cotton in the fabric is preferably at least about 35 percent by weight cotton. When employed as blends, the companion material employed in the fabric can include one or more non-cotton fibers including cellulosic or synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Stonewashing composition" means a formulation for use in stonewashing cellulose containing fabrics. Stonewashing compositions are used to modify cellulose containing fabrics prior to presentation for consumer sale, i.e., during the manufacturing process. In contrast, detergent compositions are intended for the cleaning of soiled garments.

"Stonewashing" means the treatment of cellulose containing fabric with a cellulase solution under agitating and cascading conditions, i.e., in a rotary drum washing machine, to impart a "stonewashed" appearance to the denim. The cellulase solution according to the instant invention will functionally replace the use of stones in such art recognized methods, either completely or partially. Methods for imparting a stonewashed appearance to denim are described in U.S. Pat. No. 4,832,864 which is incorporated herein by reference in its entirety. Generally, stonewashing techniques have been applied to indigo dyed cotton denim.

"Detergent composition" means a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers. Such compositions are generally used for cleaning soiled garments and are not used during the manufacturing process, in contrast to stonewashing compositions. Detergent compositions comprising cellulase are described in, for example, Clarkson et al., U.S. Pat. No. 5,290,474 and EP Publication No. 271 004, incorporated herein by reference.

"Variant" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of an enzyme variant is preferably achieved by modifying a DNA sequence which encodes for the native protein, transformation of that DNA sequence into a suitable host, and expression of the modified DNA sequence to form the derivative enzyme. The variant EGIII-like enzyme of the invention includes peptides comprising altered amino acid sequences in comparison with a precursor enzyme amino acid sequence wherein the variant EGIII-like enzyme retains the characteristic cellulolytic nature of the precursor enzyme but which may have altered properties in some specific aspect. For example, a variant EGIII-like enzyme may have an increased pH optimum or increased temperature or oxidative stability but will retain its characteristic cellulolytic activity. It is contemplated that the variants according to the present invention may be derived from a DNA fragment encoding a cellulase variant EGIII-like enzyme wherein the functional activity of the expressed cellulase derivative is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained.

"Expression vector" means a DNA construct comprising a DNA sequence which is operably linked to a suitable control sequence capable of effecting the expression of the DNA in a suitable host. Such control sequences may include a promoter to effect transcription, an optional operator sequence to control transcription, a sequence encoding suitable ribosome-binding sites on the mRNA, and sequences which control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* is cbh1. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook et al., *Molecular Cloning: A Laboratory Manual*, Second Edition, Cold Spring Harbor Press (1989). Often, such expression vectors including the DNA sequences of the invention are transformed into a unicellular host by direct insertion into the genome of a particular species through an integration event (see e.g., Bennett & Lasure, *More Gene Manipulations in Fungi*, Academic Press, San Diego, pp. 70–76 (1991) and articles cited therein describing targeted genomic insertion in fungal hosts, incorporated herein by reference).

"Host strain", or "host cell" means a suitable host for an expression vector comprising DNA according to the present invention. Host cells useful in the present invention are generally procaryotic or eucaryotic hosts, including any transformable microorganism in which expression can be achieved. Specifically, host strains may be *Bacillus subtilis, Escherichia coli, Trichodenna reesei, Saccharomyces cerevisiae* or *Aspergillus niger*. Host cells are transformed or transfected with vectors constructed using recombinant DNA techniques. Such transformed host cells are capable of both replicating vectors encoding the variant EGIII-like enzymes or expressing the desired peptide product. In a preferred embodiment according to the present invention, "host cell" means both the cells and protoplasts created from the cells of Trichoderma sp.

"Signal sequence" means a sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process.

"DNA vector" means a nucleotide sequence which comprises one or more DNA fragments or DNA variant fragments encoding an EGIII-like cellulase or variants described above which can be used, upon transformation into an appropriate host cell, to cause expression of the variant EGIII-like cellulase.

"Functionally attached to" means that a regulatory region, such as a promoter, terminator, secretion signal or enhancer region is attached to a structural gene and controls the expression of that gene.

The present invention relates to the expression, purification and/or isolation and use of variant EGIII-like cellulases. These enzymes are preferably prepared by recombinant methods utilizing the gene identified and isolated according to the methods described above. However, enzymes for use in the present invention may be obtained by other art recognized means such as purification from natural isolates.

It is conceived by the inventors that the microorganism to be transformed for the purpose of expressing an EGIII-like cellulase according to the present invention may advantageously comprise a strain derived from Trichoderma sp. Thus, a preferred mode for preparing EGIII-like cellulases according to the present invention comprises transforming a Trichoderma sp. host cell with a DNA construct comprising at least a fragment of DNA encoding a portion or all of the EGIII-like cellulase detected as described above. The DNA construct will generally be functionally attached to a promoter. The transformed host cell is then grown under conditions so as to express the desired protein. Subsequently, the desired protein product is purified to substantial homogeneity.

However, it may in fact be that the best expression vehicle for a given DNA encoding a variant EGIII-like cellulase may differ. Thus, it may be that it will be most advantageous to express a protein in a transformation host which bears phylogenetic similarity to the source organism for the variant EGIII-like cellulase. Accordingly, the present description of a Trichoderma spp. expression system is provided for illustrative purposes only and as one option for expressing the variant EGIII-like cellulase of the invention. One of skill in the art, however, may be inclined to express the DNA encoding variant EGIII-like cellulase in a different host cell if appropriate and it should be understood that the source of the variant EGIII-like cellulase should be considered in determining the optimal expression host. Additionally, the skilled worker in the field will be capable of selecting the best expression system for a particular gene through routine techniques utilizing the tools available in the art.

In one embodiment, the strain comprises *T. reesei* (*longibrachiatum*) which is a useful strain for obtaining overexpressed protein. For example, RL-P37, described by Sheir-Neiss et al. in *Appl. MicrobioL Biotechnology*, 20 (1984) pp. 46–53 is known to secrete elevated amounts of cellulase enzymes. Functional equivalents of RL-P37 include *Trichoderma reesei* (*longibrachiatum*) strain RUT-C30 (ATCC No. 56765) and strain QM9414 (ATCC No. 26921). It is contemplated that these strains would also be useful in overexpressing EGIII-like cellulases.

Where it is desired to obtain the EGIII-like cellulase in the absence of potentially detrimental native cellulolytic activity, it is useful to obtain a Trichoderma host cell strain which has had one or more cellulase genes deleted prior to introduction of a DNA construct or plasmid containing the DNA fragment encoding the EGIII-like cellulase. Such strains may be prepared by the method disclosed in U.S. Pat. No. 5,246,853 and WO 92/06209, which disclosures are hereby incorporated by reference. By expressing an EGIII-like cellulase in a host microorganism that is missing one or more cellulase genes, the identification and subsequent purification procedures are simplified. Any gene from Trichoderma sp. which has been cloned can be deleted, for example, the cbh1, cbh2, egl1, and egl3 genes as well as those encoding EGIII and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed fungus. Any selectable marker gene which is expressed in the selected microorganism will be suitable. For example, with Trichoderma sp., the selectable marker is chosen so that the presence of the selectable marker in the transformants will not significantly affect the properties thereof Such a selectable marker may be a gene which encodes an assayable product. For example, a functional copy of a Trichoderma sp. gene may be used which if lacking in the host strain results in the host strain displaying an auxotrophic phenotype.

In a preferred embodiment, a pyr4⁻ derivative strain of Trichoderma sp. is transformed with a functional pyr4 gene, which thus provides a selectable marker for transformation. A pyr4⁻ derivative strain may be obtained by selection of Trichoderma sp. strains which are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4⁻ derivative strains which lack a functional orotidine monophosphate decarboxylase enzyme and require uridine for growth by selecting for FOA resistance. Using the FOA selection technique it is also possible to obtain uridine requiring strains which lack a functional orotate pyrophosphoribosyl transferase. It is possible to transform these cells with a functional copy of the gene encoding this enzyme (Berges and Barreau, *Curr. Genet.*,19, 1991, pp. 359–365). Selection of derivative strains is easily performed using the FOA resistance technique referred to above, and thus, the pyr4 gene is preferably employed as a selectable marker.

To transform pyr4⁻ Trichoderma sp. so as to be lacking in the ability to express one or more cellulase genes, a single DNA fragment comprising a disrupted or deleted cellulase gene is then isolated from the deletion plasmid and used to transform an appropriate pyr⁻ Trichodeina host. Transformants are then identified and selected based on their ability to express the pyr4 gene product and thus compliment the uridine auxotrophy of the host strain. Southern blot analysis is then carried out on the resultant transformants to identify and confirm a double crossover integration event which replaces part or all of the coding region of the genomic copy of the gene to be deleted with the pyr4 selectable markers.

Although the specific plasmid vectors described above relate to preparation of pyr⁻ transformants, the present invention is not limited to these vectors. Various genes can be deleted and replaced in the Trichoderma sp. strain using the above techniques. In addition, any available selectable markers can be used, as discussed above. In fact, any Trichoderma sp. gene which has been cloned, and thus identified, can be deleted from the genome using the above-described strategy.

As stated above, the host strains used are derivatives of Trichoderma sp. which lack or have a nonfunctional gene or genes corresponding to the selectable marker chosen. For example, if the selectable marker of pyr4 is chosen, then a specific pyr4⁻ derivative strain is used as a recipient in the transformation procedure. Similarly, selectable markers comprising Trichoderma sp. genes equivalent to the *Aspergillus nidulans* genes amdS, argB, trpC, niaD may be used. The corresponding recipient strain must therefore be a derivative strain such as argB⁻, trpC⁻, niaD⁻, respectively.

DNA encoding the EGIII-like cellulase is then prepared for insertion into an appropriate microorganism. According to the present invention, DNA encoding an EGIII-like cellulase comprises all of the DNA necessary to encode for a protein which has functional cellulolytic activity. The DNA fragment or DNA variant fragment encoding the EGIII-like cellulase or derivative may be functionally attached to a fungal promoter sequence, for example, the promoter of the cbh1 or eg/1 gene.

It is also contemplated that more than one copy of DNA encoding a EGIII-like cellulase may be recombined into the strain to facilitate overexpression. The DNA encoding the EGIII-like cellulase may be prepared by the construction of an expression vector carrying the DNA encoding the cellulase. The expression vector carrying the inserted DNA fragment encoding the EGIII-like cellulase may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene coding region, and terminator sequence all originate from the gene to be expressed. Gene truncation may be obtained where desired by deleting away undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high level transcription and a selectable marker. It is contemplated that the coding region for a gene or part thereof can be inserted into this general purpose expression vector such that it is under the transcriptional control of the expression cassettes promoter and terminator sequences. For example, pTEX is such a general purpose expression vector. Genes or part thereof can be inserted downstream of the strong cbh1 promoter.

In the vector, the DNA sequence encoding the EGIII-like cellulase of the present invention should be operably linked to transcriptional and translational sequences, i.e., a suitable promoter sequence and signal sequence in reading frame to the structural gene. The promoter may be any DNA sequence which shows transcriptional activity in the host cell and may be derived from genes encoding proteins either homologous or heterologous to the host cell. The signal peptide provides for extracellular production of the EGIII-like cellulase or derivatives thereof. The DNA encoding the signal sequence is preferably that which is naturally associated with the gene to be expressed, however the signal sequence from any suitable source, for example an exo-cellobiohydrolase or endoglucanase from Trichoderma, is contemplated in the present invention.

The procedures used to ligate the DNA sequences coding for the EGIII-like cellulase of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in Trichoderma sp. is very low. Accordingly, uptake of the desired DNA sequence, gene or gene fragment is at best minimal. There are a number of methods to increase the permeability of the Trichoderma sp. cell wall in the derivative strain (i.e., lacking a functional gene corresponding to the used selectable marker) prior to the transformation process.

The preferred method in the present invention to prepare Trichoderma sp. for transformation involves the preparation of protoplasts from fungal mycelium. The mycelium can be obtained from germinated vegetative spores. The mycelium is treated with an enzyme which digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M to 1.2 M. It is preferable to use about a 1.2 M solution of sorbitol in the suspension medium.

Uptake of the DNA into the host Trichoderma sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the Trichoderma sp. strain and the plasmid DNA is transferred to the nucleus. This fusion frequently leaves multiple copies of the plasmid DNA tenderly integrated into the host chromosome.

Usually a suspension containing the Trichoderma sp. protoplasts or cells that have been subjected to a permeability treatment at a density of $10^8$ to $10^9$/ml, preferably $2 \times 10^8$/ml are used in transformation. A volume of 100 microliters of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if Pyr$^+$ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may be made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the EGIII-like cellulases or derivatives thereof are recovered in active form from the host cell after growth in liquid media either as a result of the appropriate post translational processing of the novel EGIII-like cellulase or derivatives thereof.

The expressed EGIII-like cellulase may be recovered from the medium by conventional techniques including separations of the cells from the medium by centrifugation, filtration, and precipitation of the proteins in the supernatant or filtrate with a salt, for example, ammonium sulphate. Additionally, chromatography procedures such as ion exchange chromatography or affinity chromatography may be used. Antibodies (polyclonal or monoclonal) may be raised against the natural purified EGIII-like cellulase, or synthetic peptides may be prepared from portions of the EGIII-like cellulase molecule and used to raise polyclonal antibodies.

Treatment of textiles according to the present invention contemplates textile processing or cleaning with a composition comprising a cellulase. Such treating includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead" cotton, from cellulosic fabric or fibers. Immature cotton is significantly more amorphous than mature cotton and results in a lesser quality fabric when present due to, for example, uneven dyeing. The composition contemplated in the present invention further includes a cellulase component for use in washing of a soiled manufactured cellulose containing fabric. For example, the cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulase is known to increase the value of animal feed, improve the drainability of wood pulp, enhance food products and reduce fiber in grain during the grain wet milling process or dry milling process.

Treating according to the instant invention comprises preparing an aqueous solution which contains an effective amount of cellulase together with other optional ingredients including, for example, a buffer, a surfactant, and/or a scouring agent. An effective amount of cellulase enzyme composition is a concentration of cellulase enzyme sufficient for its intended purpose. Thus, for example, an "effective amount" of cellulase in a stonewashing composition according to the present invention is that amount which will provide the desired effect, e.g., to produce a worm and faded look in the seams and on fabric panels. Similarly, an "effective amount" of cellulase in a composition intended for improving the feel and/or appearance of a cellulose containing fabric is that amount which will produce measurable improvements in the feel, e.g., improving the smoothness of the fabric, or appearance, e.g., removing pills and fibrils which tend to reduce the sharpness in appearance of a fabric. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be treated is added can be readily determined by the skilled artisan based on the above factors as well as the desired result. In stonewashing processes, it has generally been preferred that the cellulase be present in the aqueous treating solution in a concentration of from about 0.5 to 5,000 ppm and most preferably about 10 to 200 ppm total protein. In compositions for the improvement of feel and/or appearance of a cellulose containing fabric, it has generally been preferred that the cellulase be present in the aqueous treating solution in a concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity which, in turn, depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the final cellulase solution within the pH range required for optimal cellulase activity. The determination of the optimal pH range of the cellulases of the invention can be ascertained according to well known techniques. Suitable buffers at pH within the activity range of the cellulase are well known to those skilled in the art in the field.

In addition to cellulase and a buffer, the treating composition may optionally contain a surfactant. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated cellulase composition can be prepared for use in the methods described herein. Such concentrates contain concentrated amounts of the cellulase composition described above, buffer and surfactant, preferably in an aqueous solution. When so formulated, the cellulase concentrate can readily be diluted with water so as to quickly and accurately prepare cellulase preparations having the requisite concentration of each constituent. When aqueous concentrates are formulated, these concentrates can be diluted so as to arrive at the requisite concentration of the components in the cellulase solution as indicated above. As is readily apparent, such cellulase concentrates will permit facile formulation of the cellulase solutions as well as permit feasible transportation of the composition to the location where it will be used. The treating concentrate can be in any art recognized form, for example, liquid, emulsion, gel, or paste. Such forms are well known to those skilled in the art.

When a solid cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the cellulase composition of the present invention as desired, including stones, pumice, fillers, solvents, enzyme activators, and anti-redeposition agents depending on the eventual use of the composition.

By way of example, stonewashing methods will be described in detail, however, the parameters described are readily modified by the skilled artisan for other applications, i.e., improving the feel and/or appearance of a fabric. The cellulose containing fabric is contacted with the cellulase containing stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the cellulase enzyme to react efficiently with cellulose containing fabric, in this case to produce the stonewashed effect. However, such conditions are readily ascertainable by one of skill in the art. The reaction conditions effective for the stonewashing compositions of the present invention are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., which conditions would also be expected to be suitable for the cellulase of the invention, the optimal temperature conditions should be ascertained according to well known techniques with respect to the specific cellulase used.

Reaction times are dependent on the specific conditions under which the stonewashing occurs. For example, pH, temperature and concentration of cellulase will all effect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose containing fabrics, for example, depilling, softening, anti-pilling, surface fiber removal, anti-graying and cleaning. Preferably, the cellulase in the detergent composition is employed in a concentration of from about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase protecting agent. The granule can be formulated so as to contain materials to reduce the rate of dissolution of the granule into the wash medium. Such materials and granules are disclosed in U.S. Pat. No. 5,254,283 which is incorporated herein by reference in its entirety.

The detergent compositions of this invention employ a surface active agent, i.e., surfactant, including anionic, non-ionic and ampholytic surfactants well known for their use in detergent compositions. In addition to the cellulase composition and the surfactant(s), the detergent compositions of this invention can optionally contain one or more of the following components:

Hydrolases Except Cellulase

Suitable hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified protein. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Builders
A. Divalent Sequestering Agents.

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or Inorganic Electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as potassium monopersulfate, sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects. Similarly, bleaching agents and bleach catalysts as described in EP 684 304 may be used.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, amorphous silicas, clay, calcium silicate (such as Micro-Cell of Johns Manville Co.), calcium carbonate and magnesium oxide.

Masking Agents for Factors Inhibiting the Cellulase Activity

The cellulase composition of this invention are deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

Cellobiose, glucose and gluconolactone act sometimes as inhibitors. It is preferred to avoid the co-presence of these saccharides with the cellulase as far as possible. In case the co-presence in unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-Activators

The activators may vary depending on the specific cellulase. In the presence of proteins, cobalt and its salts, magnesium and its salts, and calcium and its salts, potassium and its salts, sodium and its salts or monosaccharides such as mannose and xylose, many cellulases are activated and their deterging powers are improved remarkably.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers The solubilizers include, for example, lower alcohols such as ethanol, benzenesulfonate salts, lower alkylbenzenesulfonate salts such as p-toluenesulfonate salts, glycols such as propylene glycol, acetylbenzene-sulfonate salts, acetamides, pyridinedicarboxylic acid amides, benzoate salts and urea The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method, agglomeration method, dry mixing method or non-tower route methods are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation or agglomeration method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose containing fabric, for example soiled fabrics, in industrial and household uses at temperatures, reaction times and liquor ratios conventionally employed in these environments. The incubation conditions, i.e., the conditions effective for treating cellulose containing fabrics with detergent compositions according to the present invention, will be readily ascertainable by those of skill in the art. Accordingly, the appropriate conditions effective for treatment with the present detergents will correspond to those using similar detergent compositions which include known cellulases.

Detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the presoak. The remainder of the composition comprises conventional components used in the pre-soak, i.e., diluent, buffers, other enzymes (proteases), and the like at their conventional concentrations.

It is contemplated that compositions comprising cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover and for depilling and antipilling (pilling prevention).

The use of the cellulase according to the invention may be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

Example 1

Preparation of Genomic DNA Encoding EGIII-Like Cellulases

Genomic DNA was prepared for several different microorganisms for the purpose of undertaking a PCR reaction to determine whether EGIII-like cellulases are encoded by the DNA for a particular organism.

Genomic DNA is obtained from *Acremonium brachypenium* deposit no. CBS 866.73; *Chaetomium brasillience* deposit no. CBS 140.50; *Chaetomium vitellium* deposit no. CBS 250.85; *Emericella desertoru* deposit no. CBS 653.73; *Fusarium equiseti* deposit no. CBS 185.34; *Gliocladium roseum* deposit no. CBS 443.65; *Humicola grisea* var. thermoidia deposit no. CBS 225.63; *Myceliopthora thermophila* deposit no. ATCC 48102–48104; *Penicillium notatum* deposit no. ATCC 9178, 9179; and *Phanerochaete chrysosporium* deposit no. ATCC 28326 and isolated according to standard methods.

PCR was performed on a standard PCR machine such as the PCT-1 50 MicroCycler from MJ Research Inc. under the following conditions:

1) 1 minute at 98° C. for 1 cycle;
2) 1 minute at 94° C., 90 seconds at 40° C., 1 minute at 72° C.
3) repeat step 2 for 30 cycles
4) 7 minutes at 72° C. for 1 cycle
5) lower temperature to 15° C. for storage and further analysis.

The following DNA primers were constructed for use in amplification of EGIII-like genes from the libraries constructed from the various microorganisms. All symbols used herein for protein and DNA sequences correspond to IUPAC IUB Biochemical Nomenclature Commission codes.

| | | |
|---|---|---|
| BOX 1: primers coding for (N/Q)NLWG | | (SEQ ID NO: 30) |
| forward primer | FRG001: AAY AAY YTN TGG GG | (SEQ ID NO: 31) |
| forward primer | FRG002: CAR AAY YTN TGG GG | (SEQ ID NO: 32) |
| BOX 1': primers coding for NNN(F/L/Y/I/L/N/K)WG | | (SEQ ID NO: 33) |

-continued

| | | |
|---|---|---|
| forward primer | FRG010: AAY AAY AAY HWI TGG GG | (SEQ ID NO: 34) |
| BOX 2: Primers coding for ELMIW | | (SEQ ID NO: 35) |
| forward primer | FRG003: GAR YTN ATG ATH TGG | (SEQ ID NO: 36) |
| reversed primer | FRG004: CCA DAT CAT NAR | (SEQ ID NO: 37) |
| BOX 2': primers coding for YELMIW | | (SEQ ID NO: 38) |
| forward primer | FRG011: TAY GAR YTI ATG ATH TGG | (SEQ ID NO: 39) |
| reversed primer | FRG012: CCA DAT CAT IAR YTC RTA | (SEQ ID NO: 40) |
| BOX 3: primers coding for GTE(P/C)FT | | (SEQ ID NO: 41) |
| reversed primer | FRG005: GTR AAN GGY TCR GTR CC | (SEQ ID NO: 42) |
| reversed primer | FRG006: GTR AAN GGY TCR GTY CC | (SEQ ID NO: 43) |
| reversed primer | FRG007: GTR AAN GGY TCY GTR CC | (SEQ ID NO: 44) |
| reversed primer | FRG008: GTR AAN GGY TCY GTY CC | (SEQ ID NO: 45) |
| reversed primer | FRG009: GTR AAR CAY TCN GTN CC | (SEQ ID NO: 46) |

PCR conditions for PWO polymerase (Boehringer Mannheim, Cat # 1644-947) comprise a 100 microliter solution made of 10 microliter of 10× reaction buffer (10× reaction buffer comprising 100mM Tris HCl, pH 8–8.5; 250 mM KCl; 50 mM $(NH_4)_2SO_4$; 20 mM $MgSO_4$); 0.2 mM each of DATP, dTTP, dGTP, dCTP (final concentration), 1 microliter of 100 nanogram/microliter genomic DNA, 1 microliter of PWO at 1 unit per microliter, 500 mM primers (final concentration) and water to 100 microliters. The solution is overlaid with mineral oil.

The PCR strategy was as follows: forward primers for BOX1 and BOX1' were combined with reversed primers from BOX3 in a mixture with the desired genomic DNA sample and run on a gel to obtain fragments in the 400–1000 base pair range. The obtained fragments were then pooled and the pool split into two approximately equal portions. The first pool was combined with the forward primers from BOX1 and BOX1' along with the reversed primer from BOX2. The second pool was combined with the forward primer from BOX2 along with the reversed primers from BOX3. Fragments having the approximate size relative to an EGIII-like cellulase considering the location of the primers within the gene, in this case corresponding to those between 250–500 base pairs, were isolated and sequenced.

From the sequenced fragments, it was possible to use the RAGE technique (rapid amplification of genomic ends) to rapidly obtain the sequence of the full length gene. Full length genes were obtained and are provided with several additional EGIII-like cellulase sequences in FIG. 3. As shown in FIG. 3, full length genes isolated from *Hypocrea schweinitzii, Aspergillus aculeatus, Aspergillus kawachii* (1), *Aspergillus kawachii* (2), *Aspergillus oryzae, Humicola grisea, Humicola insolens, Chaetomium brasilliense, Fusarium equiseti, Fusarium javanicum* (1), *Fusarium javanicum* (2), *Gliocladium roseum* (1), *Gliocladium roseum* (2), *Gliocladium roseum* (3), *Gliogladium roseum* (4), *Memnoniella echinata, Actinomycete* 11AG8, *Streptomyces lividans* CelB, *Rhodothermus mannus, Emericella desertoru,* and *Erwinia carotovara* all comprise significant homology EGIII from *Trichoderma reesei.*

Example 2

Temperature Stability Testing of EGIII and EGIII Like Cellulases

EGIII and EGIII homologs derived from *Humicola grisei, Humicola insolens, Emercella desertoru, Fusanum javanicum* and *Memnonella echinata* were tested to determine their stability under temperature stress.

Stability was assayed by following the rate of loss of activity upon incubation at a fixed, high temperature: Solutions of EGIII and EGIII-like cellulases at between 0.1 mg/ml and 0.5mg/ml in 50mM citrate/phosphate buffer at pH8.0 were incubated in a water bath at 48° C. At measured times 100 μl aliquots were removed and cooled (or frozen) rapidly. The remaining activity in these aliquots was assayed as detailed below. An irreversible thermal inactivation curve was generated by plotting remaining activity vs time, and the data fitted to a single exponential decay. The half-time of this exponential decay was determined as a measure of thermal stability. Activity assay: In a well of a 96-well micro-titer plate, 10 μl of enzyme sample was added to 120 μl of substrate (4.2 mg/ml o-Nitrophenyl Cellobioside) in 50 mM potassium phosphate, pH6.7. The plate was then incubated for 10 mins at 40° C., and the reactions then quenched with 70 μl of 0.2M Glycine. The absorption at 410 nm (due to the o-Nitrophenol released upon enzymatic cleavage of the substrate) was then measured in a micro-titer plate reader. This end-point 410 nm reading was proportional to the cellulase activity in the enzyme sample. The results of the stability testing were as follows:

| EG III LIKE ENZYME | HALF LIFE (MINUTES) |
|---|---|
| H. grisea | stable |
| H. insolens | stable |
| E. desertoru | 200 |
| F. javanicum | 93 |
| M. echinata | 192 |
| T. reesei (EGIII) | 23 |

"stable" indicates less than 20% loss in activity in 200 mins.

As can be seen by the above results, the EGIII homologs had significantly improved stability despite having relatively close homology to EGIII from *T. reesei*. Accordingly, it is apparent that these residue differences are critical for the improved stability of the EGIII homologs and, as such, further improvement of the EGIII-like cellulases by modifying these residues will result in additional incremental improvements in the stability of the EGIII-like enzymes.

We claim:

1. A variant EGIII or EGIII-like cellulase, wherein said variant comprises a substitution or deletion at a position corresponding to one or more of residues T2, S3, A8, F10, S18, A24, S25, F30, G31, V36, L38, A42, A46, D47, Q49, Q61, Q64, I65, Q69, A83, S86, S90, V109, T110, Y111, K123, D126, S133, Q134, G135, V139, T145, Q162, N164, T166, Y168, N174, R180, K183, N186, G189, V192, L193, S205, G206, N209, A211, T214 and/or I217 in EGIII from *Trichoderma reesei.*

2. The cellulase according to claim 1, said cellulase being derived from a fungus, bacteria or Actinomycete.

3. The cellulase according to claim 1, wherein said cellulase is an endoglucanase.

4. The cellulase according to claim 2, wherein said fungus is a filamentous fungus.

5. The cellulase according to claim 4 wherein said filamentous fungus belongs to Euascomycete.

6. The cellulase according to claim 5 wherein said Euascomycete is Aspergillus spp., Gliocladium spp., Fusarium spp., Acremonium spp., Myceliophtora spp., Verticillium spp., Myrothecium spp., or Penicillium spp.

7. A DNA encoding the cellulase according to claim 1.

8. A vector comprising the DNA of claim 7.

9. A host cell transformed with the vector of claim 8.

10. A method of producing a cellulase comprising the steps of:
    (a) culturing the host cell according to claim 9 in a suitable culture medium under suitable conditions to produce cellulase;
    (b) obtaining said produced cellulase; and optionally
    (c) purifying said cellulase to provide a purified cellulase product.

11. The variant EGIII or EGIII-like cellulase of claim 1, wherein said variant comprises a substitution at a position corresponding to one or more of residues T2S, S3(L/F), A8(S/D/G), F10(Y/E/A/W), S18(N/Y/L), A24(R/K/Q), S25(N/T), F30(N/E/S/W), G31Q, V36(Y/E/G), L38(S/N), A42(V/I), A46(V/T), D47(N/E/T/A), Q49(N/S/E), Q61(P/A), Q64(G/V/A), I65(R/V/Y/K), Q69(T/E/R), A83(V/W), S86(N/T/Q), S90(N/T), V109(P/E/A), T110(N/S/G), Y111(S/G/W), K123(R/A), D126(N/G), S133(Q/D/T/F), Q134(V/G/H), G135(A/S), V139(I/L), T145(N/K/S/D), Q162(P/E/S), N164(Q/D/T), T166(N/E/R), Y168(F/W), N174D, R180(Q/V/A/E), K183(R/H/Q), N186(P/S), G189(S/E), V192L, L193(I/Q/T), S205(N/D/P), G206A, N209T, A211(R/S/N), T214(S/H/R) and/or I217(Q/V/L) in EGIII from *Trichoderma reesei*.

12. The variant according to claim 11, wherein said variant comprises a substitution at a position corresponding to one or more residues A24(R/K/Q), G31Q, Q64(G/V/A), V139L, Y168F, N174D, V192L, G206A and/or N209T.

13. A DNA encoding the variant cellulase according to claim 12.

14. A vector comprising the DNA of claim 13.

15. A host cell transformed with the vector of claim 14.

16. A detergent composition comprising a surfactant and cellulase wherein said cellulase comprises a variant EGIII-like cellulase comprising a substitution or deletion at a surfactant sensitive residue at a position corresponding to one or more of residues T2, S3, A8, F10, S18, A24, S25, F30, G31, V36, L38, A42, A46, D47, Q49, Q61, Q64, I65, Q69, A83, S86, S90, V109, T110, Y111, K123, D126, S133, Q134, G135, V139, T145, Q162, N164, T166, Y168, N174, R180, K183, N186, G189, V192, L193, S205, G206, N209, A211, T214 and/or I217 in EGIII from *Trichoderma reesei*.

17. The detergent according to claim 16, wherein said detergent is a laundry detergent.

18. The detergent according to claim 16, wherein said detergent is a dish detergent.

19. The detergent composition of claim 16, wherein said variant comprises a substitution at a position corresponding to one or more of residues T2S, S3(L/F), A8(S/D/G), F10(Y/E/A/W), S18(N/Y/L), A24(R/K/Q), S25(N/T), F30(N/E/S/W), G31Q, V36(Y/E/G), L38(S/N), A42(V/I), A46(V/T), D47(N/E/T/A), Q49(N/S/E), Q61(P/A), Q64(G/V/A), I65(R/V/Y/K), 069(T/E/R), A83(V/W), S86(N/T/Q), S90(N/T), V109(P/E/A), T110(N/S/G), Y111(S/G/W), K123(R/A), D126(N/G), S133(Q/D/T/F), Q134(V/G/H), G135(A/S), V139(I/L), T145(N/K/S/D), Q162(P/E/S), N164(Q/D/T), T166(N/E/R), Y168(F/W), N174D, R180(Q/V/A/E), K183(R/H/Q), N186(P/S), G189(S/E), V192L, L193(I/Q/T), S205(N/D/P), G206A, N209T, A211(R/S/N), T214(S/H/R) and/or 1217(Q/V/L) in EGIII from *Trichoderma reesei*.

20. The detergent composition of claim 19, wherein said variant comprises a substitution at a position corresponding to one or more residues A24(R/K/Q), G31Q, Q64(G/V/A), V139L, Y168F, N174D, V192L, G206A and/or N209T.

* * * * *